United States Patent [19]

Landis

[11] Patent Number: 5,269,296

[45] Date of Patent: Dec. 14, 1993

[54] NASAL CONTINUOUS POSITIVE AIRWAY PRESSURE APPARATUS AND METHOD

[76] Inventor: Robert M. Landis, 331 E. 29th St., New York, N.Y. 10016

[21] Appl. No.: 19,993

[22] Filed: Feb. 17, 1993

Related U.S. Application Data

[63] Continuation of Ser. No. 784,371, Oct. 29, 1991, abandoned.

[51] Int. Cl.⁵ .................... A62B 7/00; A62B 9/04; A61M 15/08
[52] U.S. Cl. .................. 128/207.18; 128/204.18; 128/207.17; 128/912; 128/DIG. 26; 604/94
[58] Field of Search .............. 128/DIG. 26, 911, 912, 128/207.15, 207.16, 207.17, 207.18, 204.11, 204.12, 204.18, 200.24, 200.26, 201.22, 203.21; 604/94

[56] References Cited

U.S. PATENT DOCUMENTS

| | | | |
|---|---|---|---|
| 2,793,326 | 1/1950 | Trinder | 606/196 |
| 2,931,358 | 4/1960 | Sheridan | 128/207.18 |
| 3,481,339 | 12/1969 | Puig | 128/207.15 |
| 3,516,407 | 6/1970 | Ruggero | 606/196 |
| 3,640,282 | 2/1972 | Kamen et al. | 604/96 X |
| 3,707,151 | 12/1972 | Jackson | 128/207.15 |
| 3,766,924 | 10/1973 | Pidgeon | 606/196 |
| 3,794,036 | 2/1974 | Carroll | 128/207.15 |
| 3,850,176 | 11/1974 | Gottschalk | 606/196 |
| 3,856,051 | 12/1974 | Bain . | |
| 3,903,893 | 9/1975 | Scheer | 606/196 |
| 4,056,104 | 11/1977 | Jaffe | 128/207.15 |
| 4,090,518 | 5/1978 | Elam . | |
| 4,106,505 | 8/1978 | Salter . | |
| 4,156,426 | 5/1979 | Gold . | |
| 4,178,937 | 12/1979 | Taylor . | |
| 4,235,239 | 11/1980 | Elam . | |
| 4,273,124 | 6/1981 | Zimmerman . | |
| 4,422,456 | 12/1983 | Tiep . | |
| 4,465,067 | 8/1984 | Koch . | |
| 4,538,606 | 9/1985 | Whited . | |
| 4,709,308 | 12/1988 | Weichselbaum . | |
| 4,753,233 | 6/1988 | Grimes . | |
| 4,782,832 | 11/1988 | Trimble . | |
| 4,818,320 | 4/1989 | Weichselbaum . | |
| 4,836,200 | 6/1989 | Clark | 128/207.18 |
| 4,915,105 | 10/1990 | Lee . | |
| 5,042,478 | 8/1991 | Kopala . | |

OTHER PUBLICATIONS

"The Effect of Positive Reinforcement on Hourly Compliance in Nasal Continuous Positive Airway Pressure Users with Obstructive Sleep Apnea", E. C. Fletcher, and R. A. Luckett, Am. Rev. Respir. Dis. 1991; 143-941.

"Maxillofacial Surgery and Nasal CPAP" R. W. Riley, N. B. Powell, C. Guilleminault, Chest. 1990; 98:1421-1425.

"Surgical Treatment of Obstructive Sleep Apnea-is Mandibular Surgery an Advance?" Chest, 1990; 98:1315-1316.

(List continued on next page.)

*Primary Examiner*—V. Millin
*Assistant Examiner*—Sebastiano Passaniti

[57] ABSTRACT

A nasal continuous positive airway pressure apparatus includes a pair of cannula each having an inflatable cuff to position the cannulae within the nares of a patient. The cannulae are connected to a source of positive air pressure to provide continuous positive nasal airway pressure. The cuffs may be inflated by providing cuff apertures in the cannula so that the positive airway pressure during inhalation and exhalation maintain the cuffs inflated and the cannulae positioned within the nares during treatment. Alternatively, the cuffs may be separately inflated. The apparatus includes an inflatable air strap harness to position and hold the nasal cannulae device relative to the patient's head. The inflatable air strap harness is soft and flexible and comfortable for the patient to wear. The air strap is inflated and secured, such as with a hook and loop belt, surrounding the patient's head with the cannulae inserted into the patient's nares. The cuffs are inflated and air pressure applied to the conduit to administer treatment. The air strap is inflated by the same air pressure being applied to the patient's airway or is inflated by a separate source such as a hand pump.

19 Claims, 7 Drawing Sheets

OTHER PUBLICATIONS

"The Effect of Nightly Nasal CPAP Treatment on Underlying Obstructive Sleep Apnea and Pharyngeal Size" N. A. Collop, A. J. Block and D. Hellard, Chest. 1991;99:855-860.

"Nasal Continuous Positive Airway Pressure Facilitates Respiratory Muscle Function During Sleep in Severe Chronic Obstructive Pulmonary Disease" B. J. Petrof, R. J. Kimoff, R. D. Levy, M. G. Cosoi and S. G. Gottfried, Am. Rev. Respir. Dis. 1991, 143:928-935.

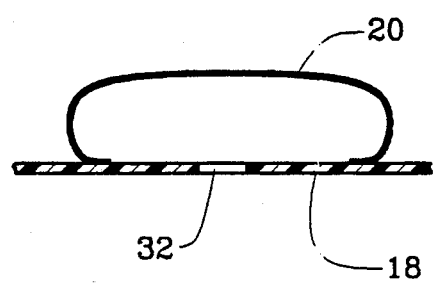
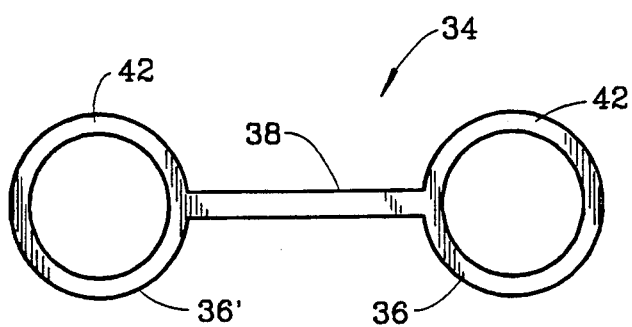
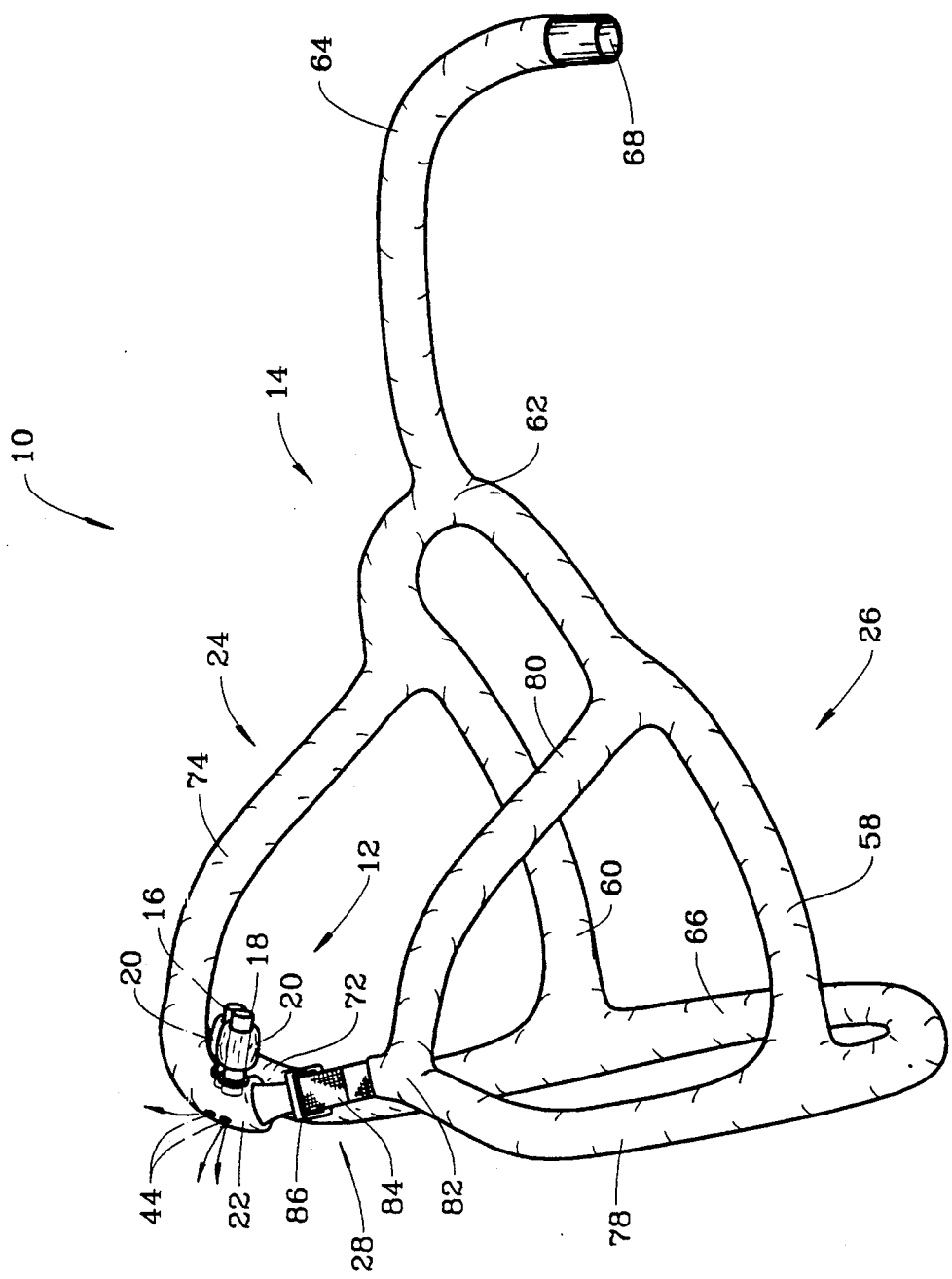

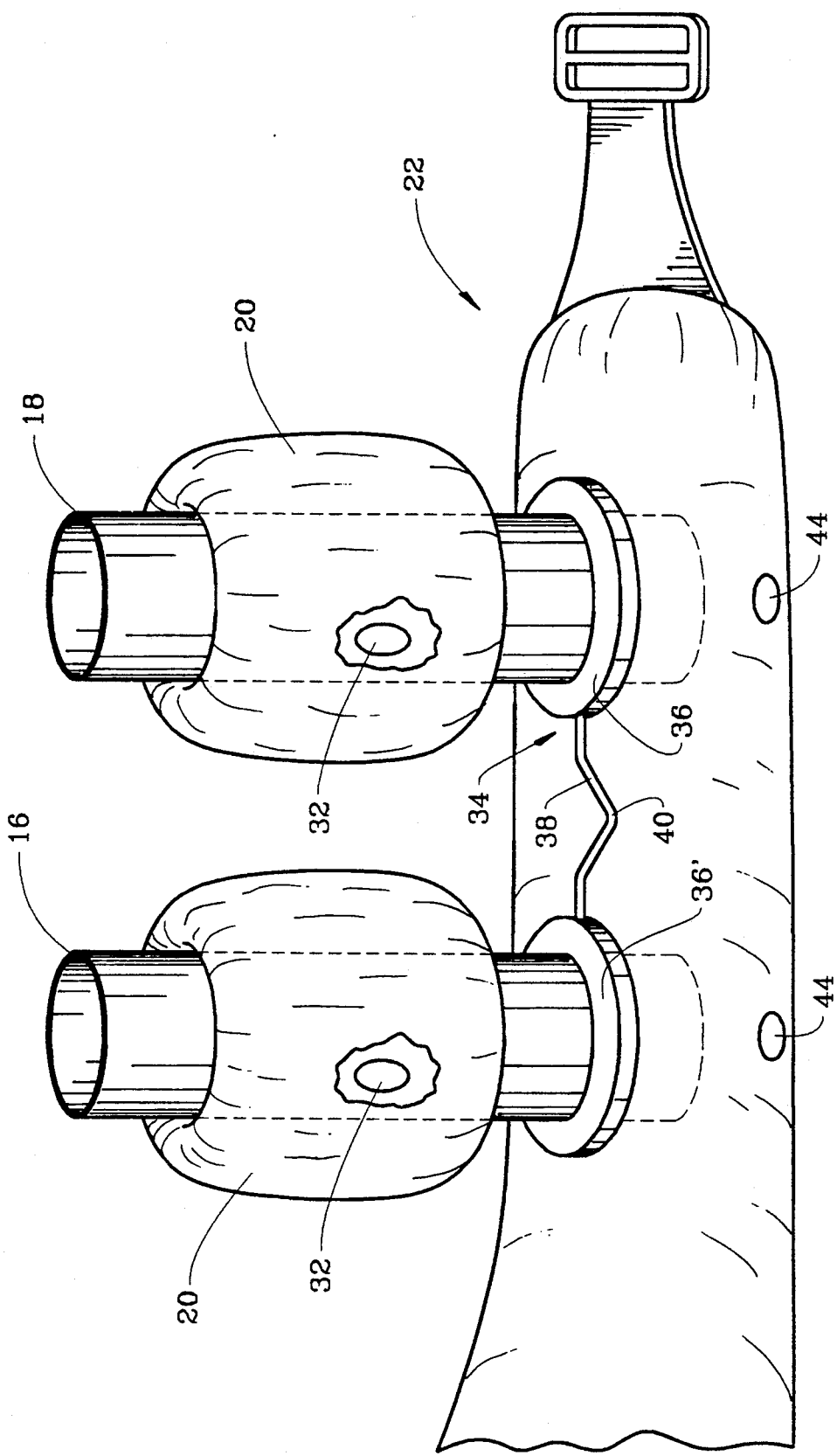

NASAL CONTINUOUS POSITIVE AIRWAY PRESSURE APPARATUS AND METHOD

This is a continuation of copending application Ser. No. 07/784,371, filed on Oct. 29, 1991 now abandoned.

The present invention relates to a method and apparatus for treating sleep apnea. More specifically, the present invention provides a nasal continuous positive airway pressure device which is reliable and comfortable to wear and therefore more acceptable to the patient.

BACKGROUND OF THE INVENTION

Obstructive sleep apnea is a condition in which the patient's airway passage is blocked and no air can pass to the lungs. During a customary sleep period a person suffering from sleep apnea can experience so called apneatic events, that is, periods when the patient's airway becomes blocked, often for ten seconds or more, until the patient rouses and starts breathing normally again. Those suffering from sleep apnea may experience hundreds of apneaic events each night causing a deficiency of restful sleep and, due to a depleted oxygen levels, possible long term health problems such as heart ailments.

Continuous positive airway pressure (CPAP) and, more specifically, nasal continuous positive airway pressure (nCPAP) has been shown to be an effective treatment for sleep apnea. See "The Effect of Nightly Nasal CPAP treatment on Underlying Obstructive Sleep Apnea and Pharyngeal Size", N. A. Collop, A. J. Block and D. Hellard, Chest 1991; 99:855–860; and "Nasal Continuous Positive Airway Pressure Facilitates Respiratory Muscle Function During Sleep in Severe Chronic Obstructive Pulmonary Disease", B. J. Petrof, R. J. Kimoff, R. D. Levy, M. G. Cosoi, and S. B. Gottfried, Am. Rev. Respir. Dis. 1991; 143:928–935. This treatment involves applying a constant gas pressure, typically a mixture of air supplemented with moisture vapor or oxygen, through the nasal passages to prevent negative pressure conditions within the passage which can lead to obstruction, thereby allowing continuous air flow through he upper air passageway. nCPAP treatment typically involves placing a mask over the nose of the patient by means of a harness or other headgear and providing a source of positive low pressure air connected to the mask. Conventional nasal masks are considered uncomfortable, cumbersome and noisy (due to air leaks) and in many cases are a formidable obstacle to patient acceptance of nCPAP therapy.

U.S. Pat. No. 4,782,832 issued to Trimble, et al. proposes an alternative device for nCPAP treatment intended to overcome the deficiencies of conventional mask devices. The Trimble structure has become the accepted apparatus for nCPAP treatment. Trimble discloses a nasal puff adapted to be worn adjacent the nose of a wearer-patient. The nasal device includes a relatively small plenum chamber including structure defining an inlet adapted for coupling with a source of gas, and a pair of spaced apart, separate gas outlets in communication with the inlet. Typically, the plenum chamber is in the form of a generally Y-shaped hollow body with the gas outlets located i the branches of the body. The nasal puff further includes a pair of gas delivery elements each having a gas flow passageway therethrough and respectively operatively coupled with a corresponding gas outlet for conveying gas from the outlet through and out the passageway. Each of the gas delivery elements is configured for insertion into a respective naris of a patient, and for this purpose the outer wall of the elements are generally frustoconically shaped so as to sealingly engage the naris-defining surfaces of the nose. Adjustability of the naris elements is provided by rotatably mounting the elements to the plenum housing and by mounting the elements in slots permitting selective lateral positioning of the elements with respect to each other. Flexible bellows-type corrugated sections can be provided in each of the elements and or in appropriate positions in the plenum housing so as to add further ranges of flexibility and adjustable. The nares elements are fabricated from relatively soft, deformable, shape-retaining synthetic resin material permitting manual deformation and alteration of the effective shape and position of the elements. Trimble discloses a harness to be worn on a patient's head with a flexible mask-retaining straps extending from the main harness strap to each side of the nasal puff. The harness assembly includes an elongated gas-conveying tube which is adapted for coupling with the inlet of the nasal puff and extends upwardly along the length of the bridge of the patient's nose and across the patient's forehead, terminating at the top of the patient's forehead. The tube is longitudinally bifurcated to divide the overall tube and present a pair of elongated, juxtaposed passageways, one of which is connected to a source of pressurized air and the other to a discharge tube for purging patient-generated $CO_2$ during exhalation.

The Trimble nasal puff and harness assembly is the accepted apparatus for treatment of sleep apnea using nCPAP therapy. While the Trimble device is a improvement over prior mask structure, some patients continue to object to the Trimble structure as uncomfortable to wear. Studies show that a small but significant number of patients fail or are unable to continue nCPAP treatment, at least some due to the inconvenience or discomfort of wearing the presently available apparatus. See "The Effect of Positive Reinforcement on Hourly Compliance in Nasal Continuous Positive Airway Pressure Users with Obstructive Sleep Apnea", E. C. Fletcher and R. A. Luckett, Am. Rev. Respir. Dis. 1991; 143:936–941; "Maxillofacial Surgery and Nasal CPAP", R. W. Riley, N. B. Powell, C. Guilleminault, Chest 1990; 98:1421–1425; and "Surgical Treatment of Obstructive Sleep Apnea—is Mandibular Surgery an Advance?", Chest 1990; 98:1315–1316.

Notwithstanding general concensus that nasal continuous positive airway pressure is an effective treatment for sleep apnea, a substantial number of patients either cannot tolerate treatment or choose to forego treatment. It is believed a substantial number of such patients could benefit from a harness and nares delivery structure which is more convenient to use and comfortable to wear, thereby resulting in increased treatment compliance.

SUMMARY OF THE INVENTION

In accordance with the present invention, an improved nCPAP system and apparatus is provided. One aspect of the invention includes at least one cannular configured and dimensioned to be loosely inserted into a patient's naris. The cannula includes an inflatable cuff with means for inflating the cuff to engage the interior walls of the nose defining the naris in order to hold the cannula in place within the naris. A source of pressurized gas, preferably air, is connected by a hose conduit to the cannula to provide nCPAP treatment.

In a preferred embodiment of the invention two cannulae with inflatable cuffs are provided; one for each naris. A resilient cannula connector also is provided for selectively positioning the cannulae with respect to each other and relative to the patient's nares. The means for inflating the inflatable cuffs may be a separate source of gas or fluid pressure connected to the cuffs, and may be connected to the cuffs through a separate inflation tube led inside or outside of the cannula. In this configuration inflation pressure may be provided by any suitable means, such as a hand activated pump. Of course, a pressure release valve must also be provided to release the inflation pressure to permit deflation of the inflatable cuffs. More preferable, cuff inflation is attained by providing cuff apertures in the side walls of the cannulae to permit communication between the lumen of the cannulae and the inflatable cuffs. The cuff apertures are configured and dimensioned to allow sufficient air pressure from each cannula lumen to enter the associated inflatable cuff to inflate the cuff and maintain the cuff in an inflated state during nCPAP treatment. Because constant pressure is provided to the cannula lumen during nCPAP treatment, such pressure must be overcome during exhalation by the patient, ensuring sufficient constant pressure within the cannula lumen to maintain the cuffs in the inflated state during both inhalation and exhalation.

The device in accordance with the preferred embodiment of the invention further includes a conduit for supplying constant gas pressure to the cannulae. The conduit preferably is made of a soft flexible material so as to minimize patient discomfort. The conduit preferable includes one or more vent apertures, such as vent holes, configured and dimensioned to relieve pressure during exhalation. The vent holes are sufficiently small in area so that the presence of the vent holes does not significantly detract from supply of pressurized gas to the cannula, yet the vent holes relieve the combined pressure of exhaled air and pressurized gas by allowing exhaled gas to exit the conduit through the vent holes. The nCPAP device may be held in place solely by the inflatable cuffs and/or by a supplemental harness for positioning the nCPAP device and conduit. A standard positioning harness may suffice, but a further aspect of the invention provides an improved harness which is more comfortable to wear and, therefore, acceptable to the patient.

The harness in accordance with the preferred embodiment of the invention is an air strap harness in which inflatable members surround and conform to the contour of the patient's head so as to maintain a constant position of the nCPAP device in a comfortable manner. The air strap includes an air hose connector attached to a primary air hose, with the air hose connector adapted to engage a source of pressurized gas used for nCPAP treatment. The primary hose branches into right and left harness segments at a Y connection, and each segment further includes a base air hose, a vertical extension hose extending substantially perpendicularly to the base air hose from a point distal to the Y connector, and an arched buttress connector hose extending from the base air hose proximal to the Y connector to a point on the vertical extension hose distal to the connection between the base air hose and the vertical extension hose. The buttress segments help provide a defined shape of the inflatable harness and ensure proper positioning of the nasal delivery device. The nCPAP device is mounted at the end of one of the vertical hose segments, and a posterior base connector hose connects the ends of the right and left base air hose segments distal to the Y connector. Securement means are provided for connecting the ends of the vertical hose segments distal to the base air hoses in order to the hold the harness around the patient's head. Preferably, all hoses of the right and left harness segments and the posterior base connector hose are made of soft inflatable plastic which inflate upon application of air pressure to the air hose connector. Advantageously, the inflatable harness itself constitutes the air conduit to the nCPAP device providing constant air pressure to the cannulae. In an alternative embodiment a separate conduit may be disposed within the harness to carry pressurized air to the cannulae. The inflatable harness is more comfortable to the user and, with the improved nCPAP device, constitutes a system which is more acceptable to the patient, resulting in greater treatment compliance. In a further alternative embodiment the inflatable harness assembly is independent of the nCPAP device and air supply and is separately inflatable, with the nCPAP delivery device secured to the harness for proper positioning.

In use, the posterior base connector hose is positioned behind the patient's neck at the base of the head with the Y connection disposed above the patient's head and the right and left harness segments to either side of the head. The nCPAP delivery device is adjusted and positioned with the cannulae in the nares, and the right and left harness segments are connected using the securement means. Typically, the vertical hose segments are disposed adjacent the cheeks of the patient and the arched buttress hose segments extend behind each ear and join the respective base air hoses. Upon activation of the air pressure source the hoses inflate to comfortably cushion the patient and provide support to the nCPAP delivery device. The securement means can be adjusted to suit patient comfort.

As used herein, the terms, "inflation" and "inflated" refer to distension of the cannula cuff to fill out the cuff without stretching the material thereof.

BRIEF DESCRIPTIONS OF THE DRAWINGS

The present invention and the disclosure herein can best be understood with reference to the accompanying drawings, in which:

FIG. 1 is a perspective view illustrating the nCPAP apparatus in accordance with the invention;

FIG. 3 is a partial perspective view in partial section illustrating an nCPAP delivery device in accordance with a second embodiment of the invention;

FIG. 4 is a partial cross-section view of the embodiment illustrated in FIG. 3;

FIG. 5 is a plan view of a cannula support;

DETAILED DESCRIPTION OF THE PREFERRED EMBODIMENTS

Figure 2:
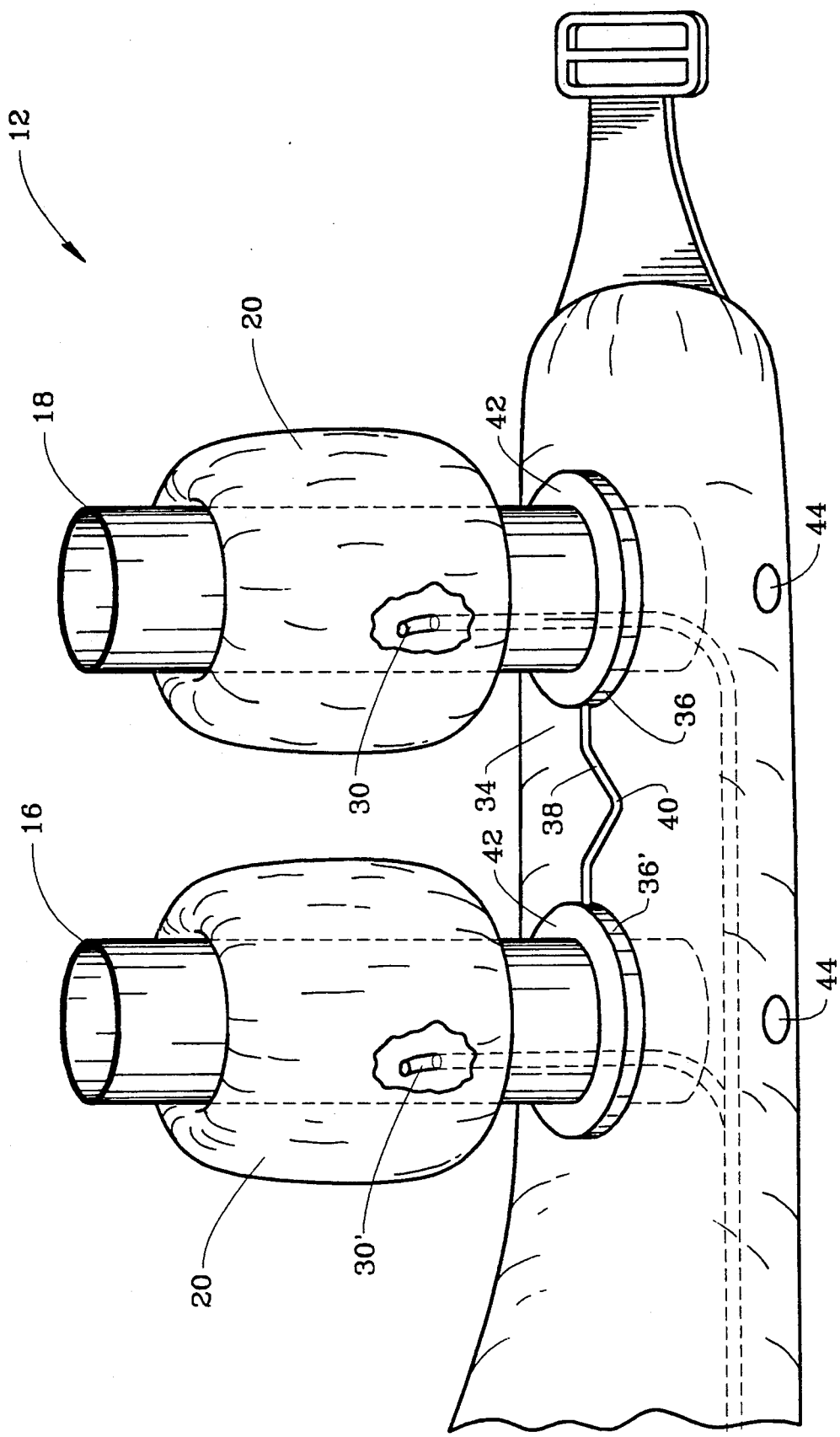
FIG. 2 is a partial perspective view in partial section illustrating an nCPAP delivery device in accordance with a first embodiment of the invention.

Referring now to the drawings, a nCPAP system 10 includes a nCPAP delivery device 12 and an air strap harness assembly 14. The nCPAP delivery device includes a pair of substantially cylindrical nasal cannulae 16, 18, each cannula has an inflatable cannula cuff 20 surrounding at least a portion of the cannula and connected to a source of inflation gas. The cannulae are mounted to a conduit 22 connected to a source of pressurized gas, preferably air, to provide nCPAP treatment in a manner to be described below. In the preferred embodiment air conduit 22 is connected to or comprises part of inflatable air strap harness 14. The harness includes right and left harness sections 24, 26 and securement means 28 for selectively and adjustably attaching the right and left harness sections together so that the air strap harness is secured surrounding a patient's head.

Referring now to FIGS. 2 and 3, each cannula is configured and dimensioned to be inserted into a naris of a patient, and typically has an outer cannula diameter about 2 millimeters (mm) to about 10 mm, and preferably about 5 mm. The cannula typically is about 10 mm to about 20 mm long and is made of a substantially rigid material such as steel or rigid plastic, e.g. styrene or vinyl plastics. The cannula can be as small as 7 or 8 french for infants. Each inflatable cuff 20 is attached to the cannula, such as by gluing, welding or the like. Cuffs 20 preferably are made of a soft, substantially has impermeable material so as to (i) maximize the degree of comfort to the sensitive nares region, and (ii) permit and retain inflation of the cuffs. Each cuff is connected to means for inflating the cuff. FIG. 2 shows a first embodiment wherein inflating tubes 30 are led through each cannula lumen and through a penetration in the cannula wall to extend into the cuff. Cuff inflation is attained by feeding pressure through tubes 30 to inflate the cuffs. In this embodiment an airtight seal is required at the point where the inflation tubes penetrate the cannulae walls. Inflation tubes 30 are connected at the distal end away from the cannulae to a source of inflation pressure (not shown) which could, for example, consist of a hand operated compression bulb or an electrical compression pump. As will be appreciated, a release valve also should be provided for selectively releasing pressure through inflation tubes 30 to deflate cuffs 30. In an alternative embodiment shown in FIGS. 3 and 4, inflation of cuffs 20 is achieved by providing cuff apertures 32 through the wall of each cannula in order to permit air flow between the cannula lumen and the cuff. One or more apertures 32 are provided in each cannula configured and dimensioned to provide optimum constant air pressure during inhalation and exhalation to inflate the cuffs at all times. Thus, during inhalation air pressure from the nCPAP positive air source flows through apertures 32 to inflate the cuffs, during exhalation pressure from the patient's breathing likewise flows through apertures 32 to inflate cuffs 20. As will be understood, the patient's exhaled breath will exceed the pressure of the nCPAP source so as to permit expulsion of gas from the lungs.

Sleep apnea treatment typically involves supplying air to the nares at about 5 to about 15 centimeters of water pressure, most typically about 10 centimeters water pressure. Positive ventilation pressure is much greater, on the order of 25 centimeters water pressure or more. The present invention preferably is constructed to operate at about 10 centimeters water pressure, but the principles of the invention also may find application at positive ventilation pressures.

In a preferred embodiment, cuffs 20 in the uninflated state are approximately 5 mm to 10 mm in length along the axial length of the cannulae. In the inflated state cuffs 20 inflate to a maximum diameter of about 12 to about 16 mm, most preferably about 14 mm, so as to conform to the nares of a patient. In the preferred embodiment wherein cuff apertures are provided between each cuff and cannula lumen, it has been determined that for a system operating at about 10 centimeters water pressure one or more apertures configured and dimensioned to provide an opening of about 12 mm$^2$ to about 16 mm$^2$ between each cuff and cannula lumen is appropriate. One aperture of about 4 mm diameter or multiple apertures of lesser diameter provide the desired opening size. Of course, different aperture dimensions may be necessary or desirable depending, for example, upon nCPAP operating pressure and/or cannula and cuff configurations and dimensions.

Referring again to FIGS. 2 and 3, the cannulae are mounted to a cannula support 34 which, in turn, is attached to air pressure conduit 22. Preferably, a substantially air tight seal is formed at the juncture of the cannula exiting from the conduit, either by forming a seal between the conduit and cannula or by forming separate seals between the conduit and support 34 and between support 34 and the cannula. In the preferred embodiment shown in FIGS. 2, 3 and 5 cannula support 34 comprises two open centered cannula receiving members 36, 36' connected to each other by a bridge member 38 (see FIG. 5). The open center of each cannula receiving member 36, 36' is configured to receive and frictionally engage a cannula, and the bridge member maintains a desired cannula separation distance. Preferably, bridge member 38 is made of a deformable material, such as metal, which can be bent and configured to permit adjustment of the cannula separation distance and attitude, i.e., parellelity of the cannulae. As shown in FIGS. 2 and 3, bridge member 38 may be provided in a slightly bent form having a knee or bend 40 to facilitate bending of bridge member 38. It is further contemplated that the cannulae should be slidable relative to cannula support member 34 so that the axial length of the cannulae extending from support 34 and air conduit 22 into the naris may be adjusted according to patient preference. Of course, it may also be desirable to provide a stop, e.g., on the cannula, to prevent the cannula from accidentally being completely withdrawn from the cannula support.

Cannula support 34 is attached to air conduit 22, such as by adhering air conduit 22 to the nasal facing surfaces 42 of cannula receiving members 36, 36'. Bridge member 38 may be left unattached to air conduit 22 in order to provide free cannula adjustment with minimal interference. Assembly of the air conduit and cannula support is a relatively simple matter. The support member is placed inside the conduit adjacent two openings corresponding to the open centers of members 36, 36' and an appropriate sealing bond is attained by gluing or welding the conduit to the support member.

Air conduit 22 includes vent holes 44 generally adjacent the cannulae for relieving excess pressure created during exhalation, and for expelling exhaled gases. Vent holes 44 are configured to relieve such excess pressure, but are small enough not sufficiently large to appreciably detract from the nCPAP treatment pressure and, hence, the cuff inflation pressure. Although not critical, it has been found that two vent holes in each cannula with each such vent hole measuring approximately 2 mm in diameter accommodates these objectives.

To use the nCPAP delivery device cannula 16,18 are positioned in a patient's nares and the position of the cannulae are appropriately adjusted by forming bridge member 38 to the desired configuration. In the embodiment shown in FIG. 2, cuffs 20 are separately inflated to hold the cannulae in place and the positive air pressure source is activated to provide positive air pressure through air conduit 22 to the cannulae lumen. In the alternative embodiment of FIG. 3, cuffs 20 are inflated simply by commencing nCPAP positive air flow, with the positive air pressure applied to the lumen of the cannulae inflating cuffs 20. During exhalation the exhaled gas overcomes the positive air pressure to permit the majority of the exhaled gas to be expelled through vent holes 44. The positive pressure of exhalation through the cannulae further maintains the cuffs in their inflated state. Advantageously, the soft flexible cuff material conforms to and comfortably accommodates variations in the nares. The cuffs further accommodate and conform to structures introduced through the nares, e.g. a nasal catheter, without compromising the positioning of the nCPAP device.

A further aspect of the invention relates to a comfortable air strap harness for retaining the nCPAP delivery device in position. Generally speaking, the harness is an air strap consisting of at least one inflatable tubular member connected at one end thereof to the nCPAP delivery device and at the other end to a source of pressurized air.

Figure 6:
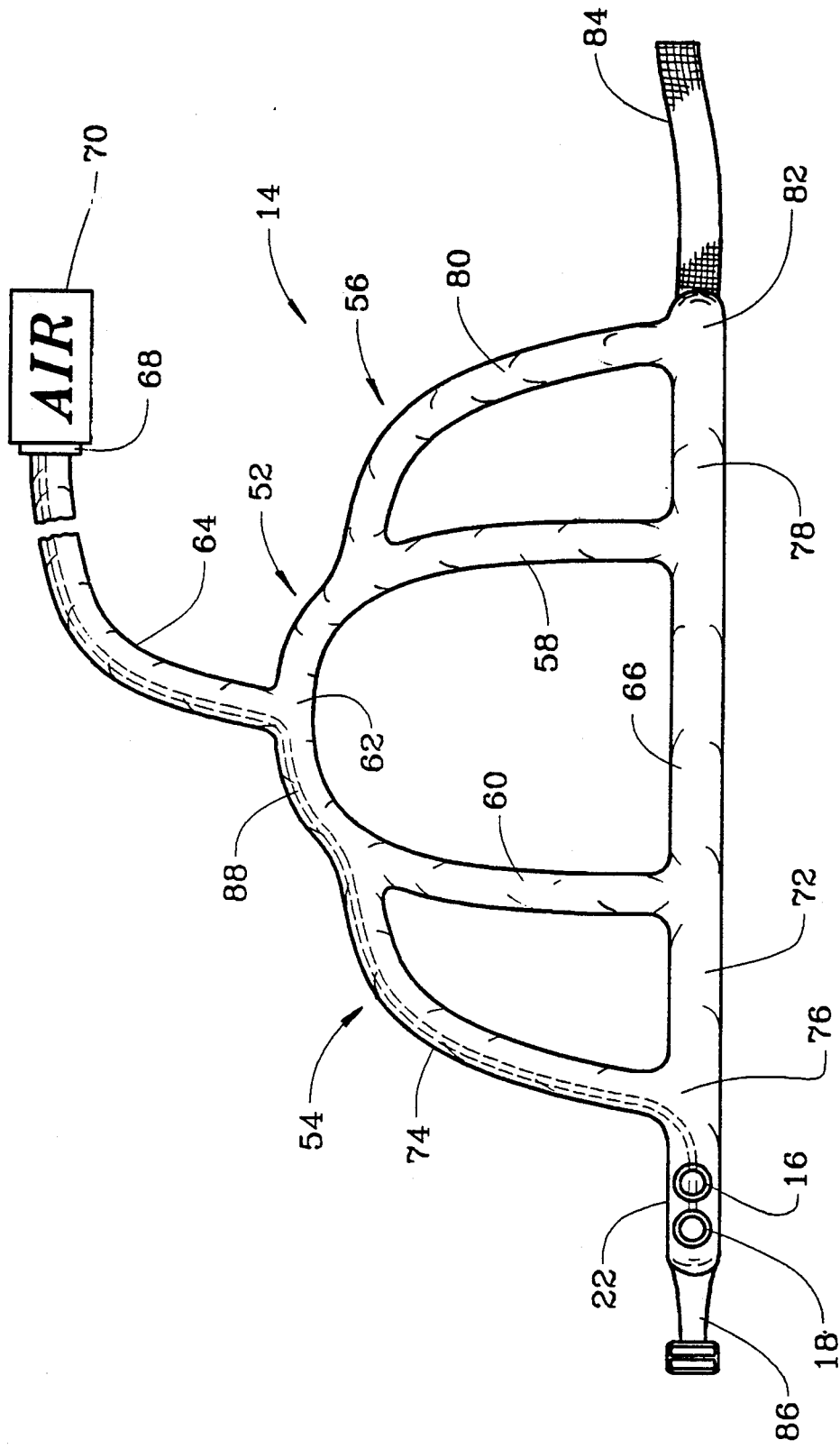
FIG. 6 is a plan view illustrating the nCPAP apparatus in accordance with a preferred embodiment of the invention.
Figure 8:
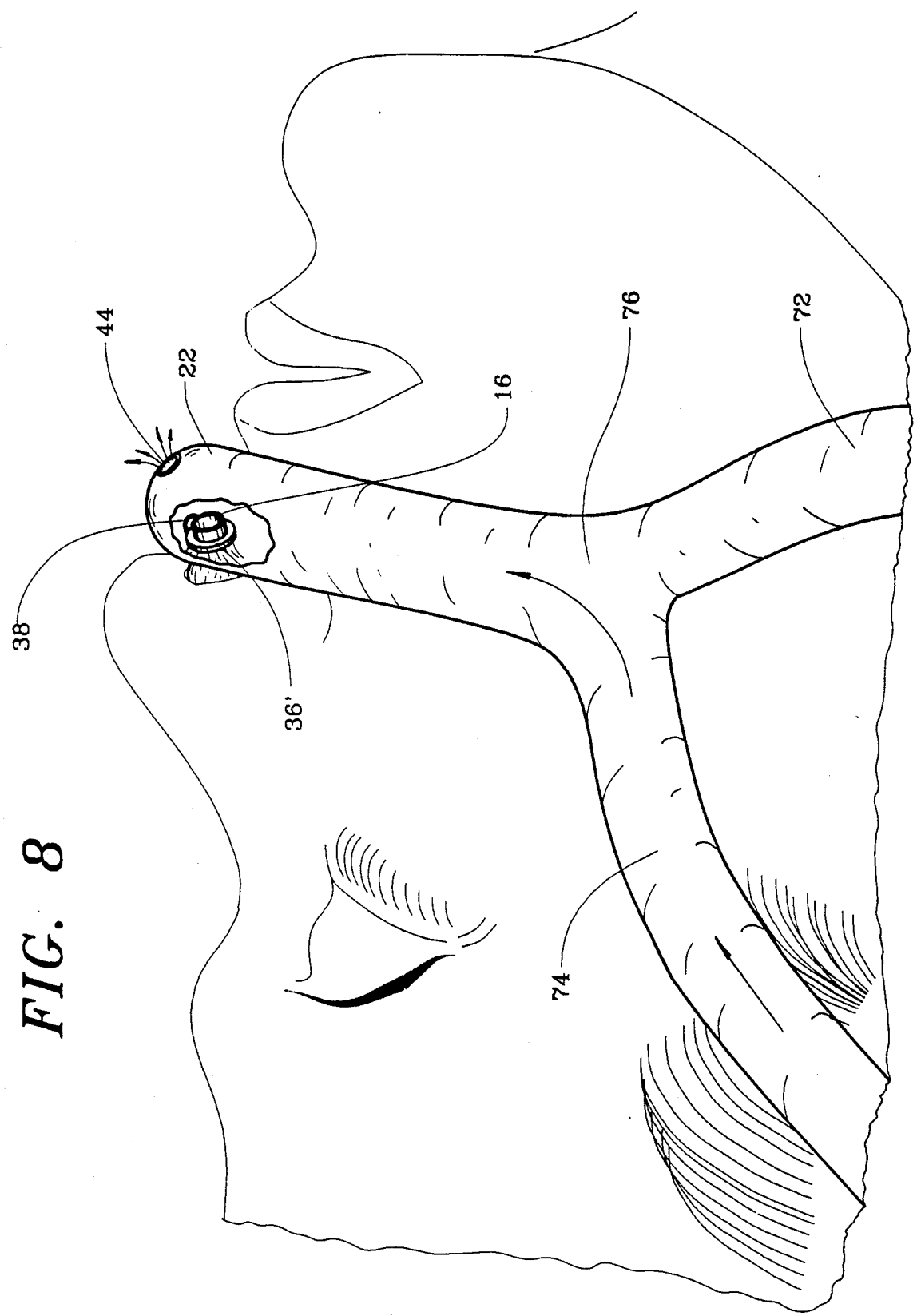
FIG. 8 is a partial elevation view in partial section of the nCPAP apparatus mounted to a patient's head with the nCPAP delivery device positioned with the cannulae within the nares.

The preferred air strap design is shown in FIGS. 1, 6 and 8. As best seen in FIGS. 1 and 6, air strap 14 includes a posterior section 52, and a right section 54, a left section 56. Posterior section 52 consists of right and left posterior inflatable segments 58, 60 joined at apex 62 to a main air supply hose 64. In addition, a posterior base inflatable connector segment 66 connects segments 58, 60 distal to apex 62. Main air supply hose 64 is provided with a connector 68 adapted to engage a standard nCPAP air pressure source 70. Right section 54 includes a base segment which may be common with right posterior inflatable segment 60, as shown, and a right cheek segment 72 connected to and extending substantially perpendicularly from right base/right posterior segment 60 at a point distal to apex 62. Right section 54 also includes a right arched buttress segment 74 connected to and extending from a point 76 on right cheek segment 72 distal to right posterior segment 60 to a point along segment 60 proximal to apex 62. Left section 56 similarly consists of a left base segment which may be common with left posterior inflatable segment 58, as shown, a left cheek segment 78 extending substantially perpendicularly from left base/posterior segment 58 and a left arched buttress segment 80. The left arched segment is connected to left cheek segment 78 at a point 82 distal to left base/posterior segment 58 and extends to a point on left base/posterior segment 58 proximal to apex 62. Adjacent point 82 a first securement member 84 is attached to left section 56. Air conduit 22 is connected to right arched segment 74 and right cheek segment 72 at about point 76 and extends therefrom. As described, air conduit 22 supports the nCPAP cannulae and delivers pressurized air to the nCPAP cannulae lumen. The end of conduit 22 has attached thereto a second securement member 86 adapted to engage first securement member 84. The securement means may be a hook and loop, e.g., Velcro, type belt structure insertable through a belt loop on second securement member 86. Thus, one side of a belt may be provided with a hook and eye fastener so that the hooks and eyes may be engaged to hold the harness in place by passing the belt through a corresponding belt loop on second securement member 86 and doubling the belt back upon itself. Alternatively, snap, buckle or other structures could be used.

In accordance with the preferred embodiment of the invention at least one, and preferably all of the soft inflatable segments communicates with main air hose 64 and conduit 22 in order to deliver pressurized air to the cannulae. Most preferably, all segments of an air strap 14 are made of a soft inflatable material which inflates to comfortably surround a patient's head in response to nCPAP treatment pressure. In order to prevent accidental collapse of any harness segments, which collapse might undesirable disrupt or interfere with delivery of air to conduit 2 and cannulae 16, 18, it is contemplated that one or more of the inflatable hose may be corrugated to provide ridigity and, perhaps, to permit positional adjustment of the tube. It is further contemplated that a substantially rigid inner air supply hose 88 (shown in phantom in FIG. 6) may be provided to assure continuous and uninterrupted air pressure to conduit 22. As will be appreciated, all inflatable segments are inflated by air applied to the air source connector and fed through the inflatable members to conduit 22 and cannulae 16, 18. Alternatively, the inflatable members may be inflated separately from the air supply to the conduit and cannulae.

Figure 7:
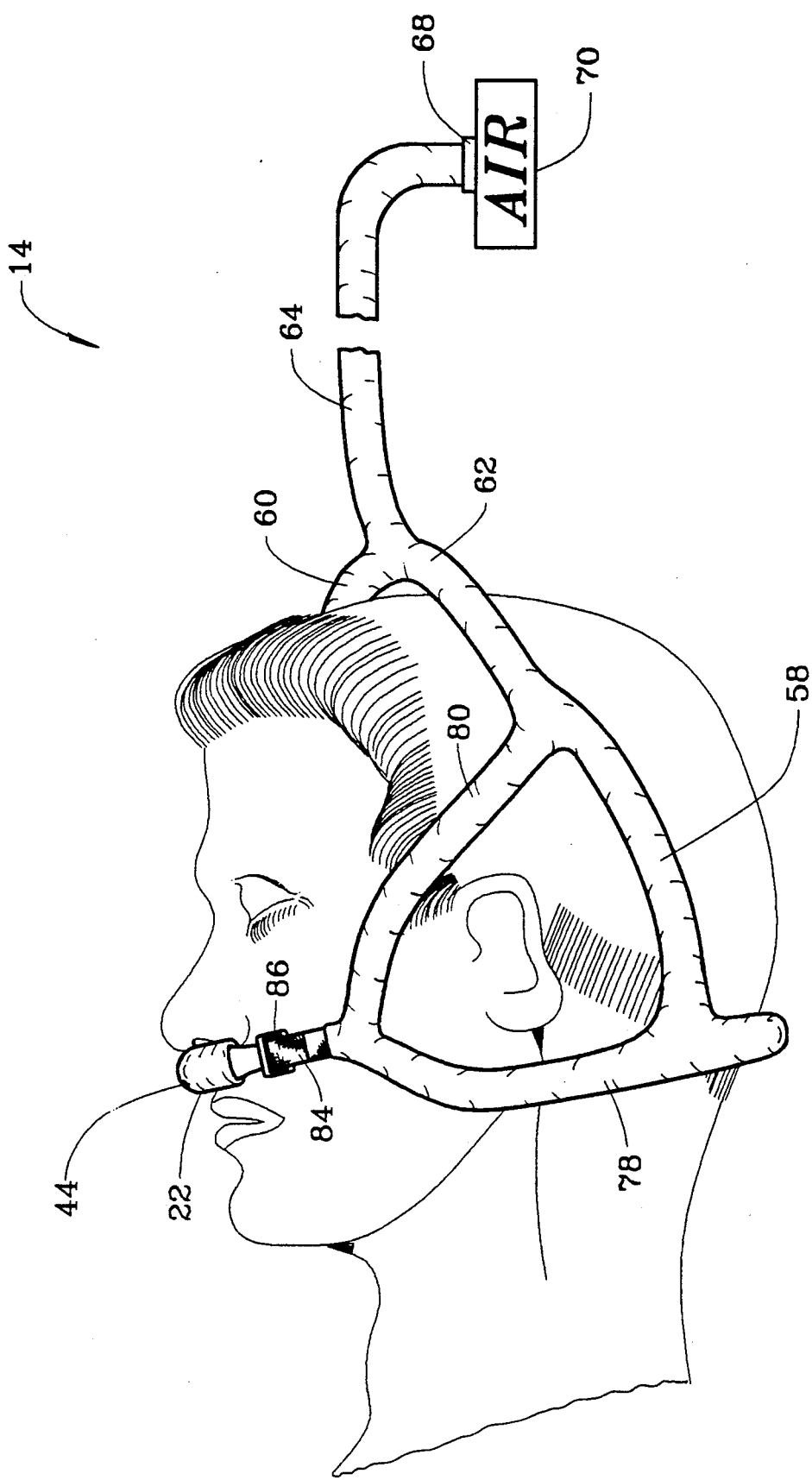
FIG. 7 is an elevation view of the nCPAP apparatus in the operative position mounted to a patient's head.

In use, posterior harness section 52 is positioned behind a patient's head with posterior base connector segment 66 disposed adjacent the patient's neck and Y connection 62 above the head (see FIG. 7). Right and left harness sections 54, 56 are brought adjacent to the sides of the patient's head, as illustrated in FIGS. 1 and 7, and cannulae 16, 18 are inserted into the nares and adjusted to the desired position by manipulating bridge member 38. First and second securement members 84, 86 are engaged to hold the harness in place. Cuffs 20 are separately inflated, if necessary, and the air source is activated to inflate the air strap and commence nCPAP treatment. In the preferred embodiment shown in FIG. 3, nCPAP air pressure inflates the cuffs and holds the cannulae in place in the patient's nares. During exhalation, the cuffs are also maintained inflated as described and exhaled gases and pressure are released through vent holes 44.

As will be appreciated, both the nasal cannulae and cuff configuration of the preferred nCPAP delivery device and the configuration and construction of the soft inflatable air strap substantially improve patient comfort and treatment compliance.

Figure 9:
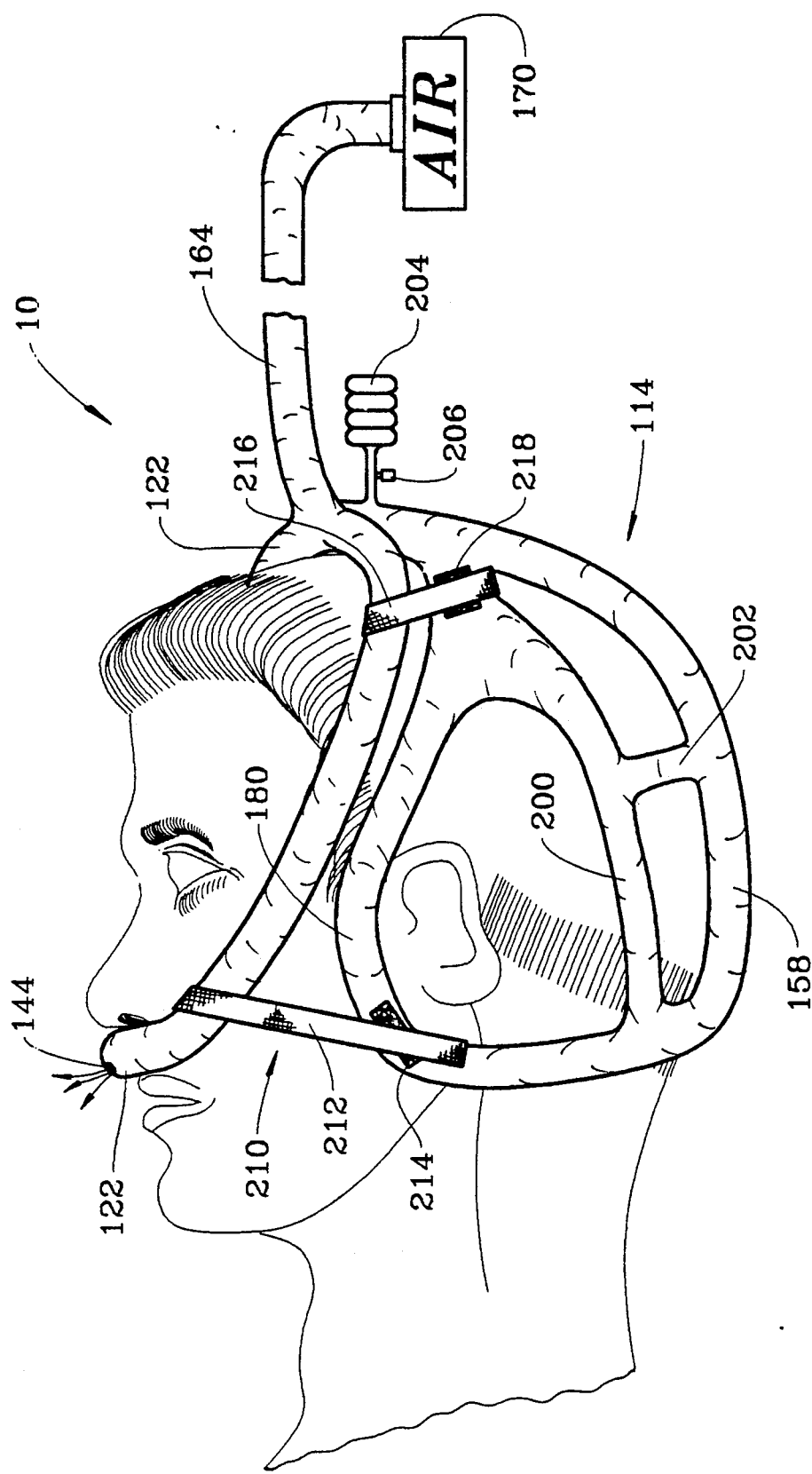
FIG. 9 is a perspective view illustrating a fourth embodiment of the invention wherein the air strap harness is inflatable independent of the nCPAP treatment air supply.

In an alternative embodiment shown in FIG. 9, air strap harness 14 is independent of and separate from the conduit 22 and nCPAP air supply. Such a configuration may be desirable where the air pressure supplied to the patient is either insufficient to maintain the inflation of the air strap or exceeds the inflation pressure of the air strap. This separatable configuration may also be desirable since various combinations of harness and delivery device can be offered. Thus, variously sized harnesses can be offered in combination with variously sized delivery devices with reduced inventory since any size harness could be used with any given delivery device. By way of example, delivery devices having a range of cannulae diameter could be maintained to suit patient comfort, and could be coupled with any one of a number of different size harnesses. This would allow the physician to maximize patient comfort with a reduced inventory of devices.

Referring again to FIG. 9, air conduit 122 extends to and communicates directly with main air supply hose a64 which, in turn, is connected to nCPAP air pressure source 170. As shown, conduit 122 may extend around both sides of the patient's head. Conduit 122 is provided with an nCPAP delivery device (not shown) to be positioned in the patient's nares, and includes vent holes 144 adjacent the patient's nares to expel excess gas. Air strap 114 is similar to air strap 14 shown in FIG. 1, including buttress segments and posterior segments. Left buttress segment 180 and left posterior segment 158 are visible in FIG. 9. The harness o9f FIG. 9 is shown to include additional side segments 200, 202 for added support. In contrast to prior embodiments, however, the air strap harness of FIG. 9 does not communicate with nCPAP air supply 170, but rather is attached to an independent harness inflation source 204, shown as a hand operated inflation bulb with a deflation control valve 206. Of course, the harness inflation source could also be an automatic supply, such as an electric air compressor, and could further include an automatic pressure sensitive control circuit. As shown in FIG. 9, conduit 122 has attached to it at least one fastening belt arrangement 210, preferably consisting of a belt 212 with loops of a hook and loop fastener system. A corresponding hook strap 214 is attached to harness 114, shown in FIG. 9 attached to buttress section 180. At least one corresponding conduit - air strap attachment is provided on the opposite side of the patient's head to provide optimum positioning of the nCPAP delivery device, conduit 122 and harness 114. It may also be desirable to provide additional conduit - harness attachment for added security, shown in FIG. 9 as loop strap 216 attached to conduit 122 toward the top of the patient's head and engaging corresponding hook strap 218 secured to harness 114. As in prior embodiments, other means of attachment such as buckles, snaps etc. may also be used to secure the nCPAP delivery device to air strap harness 114.

While the foregoing description contains many specifics, alternative constructions, configuration and embodiments will become apparent through practice with the invention, all within the scope of the appended claims. By way of example only, and without limitation, the air strap configuration may be altered to conform to and accommodate variations in the size and/or shape of the patients s head. It is also contemplated that it may be desirable to provide multiple sizes of the air stap and nCPAP delivery device in order to accommodate patient's ranging from infants to large adults.

What is claimed is:

1. A nasal airway pressure device comprising:
   a pair of naris cannulae made of a substantially rigid material, each said cannulae configured and dimensioned for insertion into the naris of a patient and having a lumen;
   a pair of inflatable cuffs, each said cuff surrounding at least a portion of one of said cannulae, each said cuff configured and dimensioned to inflate and come into contact with the interior, naris defining walls of a patient's nose so as to maintain the position of a portion of said cannulae within a naris of a patient and establish a substantially air-tight seal between said cannular portion and the naris, a second portion of said cannulae configurated and dimensioned to extend out of the naris;
   at least one aperture providing gaseous communication between said cannulae lumen and said inflatable cuff for inflating said inflatable cuffs;
   a conduit in communication with said lumen at said second cannular portion for supplying positive gas pressure to said lumen, said positive gas pressure inflating said cuffs through said aperture during inhalation by the patient so that said cuffs engage the interior walls of the patient's naris in order to maintain the position of said cannulae in the naris and establish a substantially air-tight seal between said cannulae and the naris, said cuffs being inflated during exhalation of the patient by exhaled gas expelled through said cannulae in communication with said aperture, said conduit including at least one vent hole for relieving excess pressure during exhalation.

2. The device of claim 1 wherein said means for providing gaseous communication comprises at least one aperture through a wall of said cannulae.

3. The device of claim 1 further comprising means for providing continuous positive pressure to said conduit.

4. The device of claim 1 further comprising means for adjusting the relative position of said cannulae.

5. The device of claim 4 wherein said means for adjusting the relative position of said cannulae comprises a resilient member connected to each said cannulae.

6. The device of claim 5 wherein said resilient member is made of metal.

7. The device of claim 1 further comprising a harness for supporting the device on the head of a patient.

8. The device of claim 7 wherein said harness comprises at least one inflatable tubular member and means for securing said inflatable tubular member with respect to a patient's head.

9. The device of claim 7 wherein said harness comprises:
   at least two flexible inflatable tubular members configured and dimensioned to be disposed on either side of a patient's head, said flexible members connected at an apex to an air supply tube, a connecting member attaching said inflatable tubular members distal to said apex and securing means releasably connecting said tubular members around a patient's head to support said cannular in the patient's naris.

10. The apparatus of claim 1 wherein said material is steel.

11. The apparatus of claim 1 wherein said material is plastic.

12. The apparatus of claim 1 wherein said cuffs are made of a soft flexible material.

13. A nasal airway pressure device comprising:
    at least one naris cannular having a lumen;
    an inflatable cuff surrounding at least portion of said cannulae within a naris of a patient and establishing a substantially air-tight seal between said cannular and the naris;
    means for inflating said inflatable cuff;
    conduit means in communication with said lumen for supplying positive gas pressure to said lumen; and a harness of at least two flexible inflatable tubular members configured and dimensioned to be disposed on either side of a patient's head, said flexible members connected at an apex to an air supply tube, a connecting member attaching said inflatable tubular members distal to said apex and securing means releasably connecting said tubular members around a patient's head to support said cannular in the patient's nares, said at least two flexible inflatable members and said connecting member being hollow inflatable members in gaseous communication with each other and said supply tube and said conduit means, said flexible inflatable tubular members and said connecting member being inflated and said lumen being supplied with positive gas pressure when positive air pressure is supplied to said air supply tube.

14. A method of providing nasal positive airway pressure comprising:
   providing a pair of nasal cannular, each said cannular having inflatable cuff means surrounding a portion thereof and configured and dimensioned to inflate into contact with the interior, naris defining, walls of a patient's nose, each said cannular having a lumen and at least one aperture providing gaseous communication between said cannular lumen and said inflatable cuff means, said cannulae and cuff configured and dimensioned to be inserted into a naris of a patient;
   inserting each said cannulae into a naris of a patient; and
   supplying positive air pressure to said cannulae lumen to provide nasal positive airway pressure, said positive air pressure inflating said cuffs during inhalation by the patient so that said cuffs engage the interior walls of the patient's naris in order to maintain the position of said cannulae in the naris and establish a substantially air-tight seal between said cannular and the naris, said cuffs being inflated during exhalation of the patient by exhaled gas expelled through said cannulae.

15. The method of claim 14 wherein said step of supplying positive air pressure to said cannulae comprises;
   providing an inflatable air strap harness connected to and in gaseous communication with said cannulae and a source a positive air pressure; and
   activating said source of positive air pressure.

16. A harness for securing a nasal air supply device to a patient's head comprising:
   a first inflatable flexible member having a proximal portion, a distal base portion and a leg portion;
   a second inflatable flexible tubular member having a proximal portion, a distal base portion and a distal leg portion, said first member base portion and said second member base portion attached to each other, said first and second member base portions connected to each other by an inflatable flexible tubular connecting member in gaseous communication with at least one of said flexible tubular members;
   means for releasably securing said first member leg portion to said second member leg portion, at least one of said flexible tubular members supporting a nasal air supply device; and
   means for inflating said first and second tubular members about a patient's head to secure a nasal air supply device relative to the patient's head.

17. The device of claim 16 wherein said releasable securing means comprise a buckle.

18. The device of claim 16 wherein said releasable securing means comprise a hook and loop fastener.

19. A harness for securing a nasal air supply device to a patient's head comprising:
   a first inflatable flexible member having a proximal portion, a distal base portion and a leg portion;
   a second inflatable flexible tubular member having a proximal portion, a distal base portion and a distal leg portion, said first member base portion and said second member base portion attached to each other, said first and second inflatable flexible tubular members including a buttress portion connecting said distal leg portions to said proximal portions;
   means for releasably securing said first member leg portion to said second member leg portion, at least one of said flexible tubular members supporting a nasal air supply device; and
   means for inflating said first and second tubular members about a patient's head to secure a nasal air supply device relative to the patient's head.

* * * * *